United States Patent [19]

Littlefield et al.

[11] Patent Number: 5,093,259
[45] Date of Patent: Mar. 3, 1992

[54] CONTINUOUS CELL-LINE TAMARIN ADENOCARCINOMA OF THE COLON

[75] Inventors: Lynda G. Littlefield, Clinton; Shirley P. Colyer, Kingston, both of Tenn.

[73] Assignee: Oak Ridge Associated Universities, Inc., Oak Ridge, Tenn.

[21] Appl. No.: 216,892

[22] Filed: Jul. 7, 1988

[51] Int. Cl.$^5$ .............................................. C12N 5/06
[52] U.S. Cl. .............................. 435/240.2; 435/240.31
[58] Field of Search ...................................... 435/240.2

[56] References Cited

PUBLICATIONS

Yaniv et al. (1978), Expl. Cell Biol., vol. 46, pp. 220–230.
Quinn et al. (1979), Cancer Research, vol. 39, pp. 4914–4924.
Drewinko et al. (1976), Cancer Research, vol. 36, pp. 467–475.
Semple et al. (1978), Cancer Research, vol. 38, pp. 1345–1355.
McCombs et al. (1976), Cancer, vol. 38, pp. 2316–2327.
Tom et al. (1976), In Vitro, vol. 12, No. 3, pp. 180–192.

*Primary Examiner*—Elizabeth C. Weimar
*Assistant Examiner*—George C. Elliott
*Attorney, Agent, or Firm*—Birch, Stewart, Kolasch & Birch

[57] ABSTRACT

The present invention relates to a continuous cell-line tamarin adenocarcinoma of the colon derived from the species *Saquinus oedipus oedipus* which is designated TAC-1. The invention is also directed to a method for establishing an adenocarcinoma cell-line, which comprises, obtaining a sample of a colorectal tumor, and then mincing, incubating and subculturing the sample. Finally, the invention is directed to a method for the serial passage of the cell-line and a suitable medium therefor.

4 Claims, No Drawings

CONTINUOUS CELL-LINE TAMARIN ADENOCARCINOMA OF THE COLON

FIELD OF THE INVENTION

The present invention relates to methodologies employed in establishing an adenocarcinoma cell line (TAC-1) in culture, the TAC-1 cell-line per se and biologically pure cultures thereof, specific methods used for serial passage of the cell-line, and results of various cytological, histochemical and microscopic evaluations that characterize the adenocarcinoma cell-line.

BACKGROUND OF THE INVENTION

Colorectal cancer is one of the leading causes of death in North America, with the number of new cases of this disease ranked second only to the number of new cases of lung cancer [American Cancer Society, Vol 38, Jan. and Feb. (1988), p.15]. In spite of its prevalence among humans, spontaneous adenocarcinoma of the colon appears to be quite rare in other mammalian species, including primates. A notable exception is the high incidence of spontaneous colonic carcinomas in the cotton-top tamarin, *Saquinus oedious oedipus*.

The malignancy was first identified in tamarins housed at the Oak Ridge Associated Universities (ORAU) Marmoset Colony in the late 1960's [Lushbaugh et al., Prim. Med; Vol. 10, pp. 119-134 (Karger, Basel 1978)]. Subsequently, in excess of 190 cases of colorectal adenooaroinoma have been diagnosed in 11 separate animal facilities housing colonies of *S. oedious* primates (Clapp, 1988, unpublished informal survey). Detailed descriptions of the colon pathology and histological characteristics of the tamarin colon cancer have been presented (Lushbaugh, et al, Ibid., 1978; Swartzendruber and Richter, Lab. Invest., Vol. 43, No. 6, 1980, pp. 523-529; Lushbaugh, et al.; Dig. Dis. and Sci., New Series Vol. 30 No. 12, Dec. 1985, pp. 119S-125S; and, Clapp, et al., Ibid., 1985). Briefly, the cancer appears to arise at the base of colonic crypts, and progresses into poorly-defined colonies which may displace other cells for the full thickness of the mucosa, prior to forming a malignant ulcer. The cancer is multicentric in origin, and metastasizes to mesenteric lymphatic channels and nodes quite commonly. Histologically, the carcinoma is poorly differentiated, comprising highly mitotic stem-cells, mucin-producing cells, argentaffin cells and absorbtive cells in various stages of differentiation. Cells are easily stained with the PAS stain, which demonstrates that some of the malignant cells always produce mucin. In the animal, PAS positive neoplastic cells are detectible in primary sites, lymphatics and secondary sites. These cells exhibit fine granularity of the cytoplasm, intracytoplasmic cysts with positive mucin content, and typical goblet or signet ring mucin-secreting cells.

Adenocarcinoma of the colon in tamarins resembles the human disease in "unknown etiology, epithelial cell types involved, apparent relationship to chronic colitis, local invasiveness, and propensity for easily metastatic spread", as discussed by Lushbaugh et al. (Comp. Pathol. Bull. Vol. 15, pp. 2-4, 1983). Indeed, the spontaneous appearance of colorectal adenocarcinoma in the cotton-top tamarin has been proposed as an animal model for the human disease (Lushbaugh et al., Ibid., 1983; Clapp et al., in Carcinoma of the large Bowel and Its Precursors, pp. 247-261, Alan r. Liss, Inc., 1985). Because of the uniqueness of this primate cancer, considerable efforts have been made by several laboratories to establish continuous cell-lines from tumor material of affected animals. Although methodology has been described for the initiation of cell-lines from colorectal adenocarcinomas from several species, including rats (Borman et al., Cancer Res., Vol. 42, pp. 6074-6083, Dec. 1982); mice (Tan et al., J. Nat. Cancer Inst., Vol. 56 No. 4, pp. 871-873, Apr. 1976); guinea pigs (O'Donnell and Cockerell, Cancer Res. Vol. 41, pp. 2372-2377, June 1981), and human tumors (Tomkins et al., J. Nat Cancer Inst., Vol. 52 No. 4, Apr. 1974; Willson et al., Cancer Res., Vol. 47, pp. 2704-2713, May 15, 1987; Whitehead et al., Cancer Res., Vol. 47, pp. 2683-2689, May 15, 1987), earlier attempts to culture biopsies of the tamarin colorectal tumor have uniformly met with failure.

SUMMARY OF THE INVENTION

Accordingly, one object of the present invention is to provide a continuous cell-line tamarin adenocarcinoma of the colon derived from the species *Saquinus oedipus oedipus* which is designated TAC-1 and is useful as a research tool such as in basic cancer research.

Another object of the present invention is to provide methodologies employed in establishing TAC-1 in culture as well as specific methods used for serial passage of the cell-line and a suitable medium therefor.

Results of various cytological, histochemical and microscopic evaluations that characterize the tamarin adenocarcinoma cell-line are also disclosed.

DESCRIPTION OF THE PREFERRED EMBODIMENTS

The present invention relates to an adenocarcinoma cell-line derived from a biopsy of tumor tissue from an affected tamarin (species *Saquinus oedipus oedipus*). The present invention is also related to methodologies used in establishing and propagating the cell-line in vitro. The cell-line, which is designated TAC-1, has been maintained in culture for eight months, and successfully passaged 19 times. TAC-1 has been deposited with the Americal Type Culture Collection in accordance with the provisions of the Budapest Treaty and designated ATCC CRL 10632.

The cells typically grow in cultures in "grape-like clusters" of tightly adhering spheroid cells that are resistant to mechanical disruption and proteolytic enzyme digestion. These cell clusters are free-floating in the medium, or loosely attached to the surface of underlying fibroblast monolayers. The TAC-1 cells cannot be propagated or serially passaged in the absence of a "feeder" layer of apparently normal fibroblasts which simultaneously grew out from the tumor biopsy. TAC-1 cells are aneuploid, typically exhibiting eight additional chromosomes in excess of the diploid complement of 46. Histologically, the cultured cells exhibit numerous features characteristic of the tamarin colon cancer cells in vivo, including strong PAS-positivity, and the "signet ring" morphology that is typical of goblet cells in vivo. The TAC-1 cells have been shown to be tumorogenic in one of four trials in nude mice. The cell-line will provide unique research material for basic research studies in tumor cell biology.

Methods Used To Establish TAC-1 Culture

A biopsy of a colorectal tumor was obtained during a proctoscopic examination of a six-year-old male *S. oedi-*

*pus* tamarin. The large "napkin ring" rectal tumor was located approximately 3cm from the anus and partially occluded the descending colon. The sample comprised several small (<1mm²) and one large (~2mm²) pieces. After receipt in the tissue culture laboratory, the biopsy fragments were washed eight times in Hanks' Balanced Salt Solution (HBSS), and transferred to a Petri dish containing ~2ml HBSS. The tissue was finely minced with a scalpel and transferred into a 25 cm Falcon primaria flask containing 5ml complete medium (RPMI 1640 supplemented with 10% fetal bovine serum, 100 units/ml penicillin, 100μg/ml streptomycin, 2mM L-glutamine and 2.5μg/ml fungizone). The flask was incubated at 37° C. in a 5% $CO_2$ incubator for several months. Within 24 hours, several tissue fragments had loosely adhered to the bottom of the flask, and an additional 5 ml of complete medium was added. Within the first week, scattered foci of cells having typical fibroblast morphology were observed. During the next six weeks, the culture media was changed at intervals of four-to-five (45) days. Furthermore, during this time period, the spent medium was discarded and no attempt was made to preserve any floating cells or non-adherent tissue fragments. On day 43 after inoculation of the tumor fragments into the tissue culture flask, the fibroblast monolayer had reached confluency and the cells were trypsinized by standard methods and subcultured at a ratio of 1:2 (e.g. the contents of the flask were split into two (2) portions). Ten days after the second subculture, unusual clusters of floating spheroid cells were observed in the culture medium. During the next seven passages, the medium containing the floating cells was conserved and both cell types were subcultured simultaneously. After the eighth subculture, (approximately four months after initiation of the primary culture) the colonies of floating cells were quite numerous and sufficient material was available to attempt preliminary characterization of the cell type.

A. Gross Appearance In Culture

In culture, the round, light-refractile cells typically grow in clusters or aggregates that are free-floating in the medium, or loosely attached to the surface of the underlying fibroblast monolayer. The number of cells in individual floating "colonies" varies from pairs of cells to exceedingly large clusters containing hundreds to thousands of tightly-adhering spheriod cells. The characteristic morphology of the TAC-1 cells in culture appears to be quite similar to that described for two human colorectal cancer cell-lines, i.e., VACO 5 and 4S, which are described as "disorganized, grape-like, multicellular aggregates" (McBain et al., Cancer Res., Vol. 44, pp. 5813-5821, 1984).

B. Cytological and Histochemical Studies

Cytospin slides were prepared from floating cells obtained from cultures in their eighth and tenth passages. These histological preparations of TAC-1 cells also reveal aggregates of between two and several hundred cells with no definitive pattern in their arrangement. The clusters typically contain a heterogeneous population of spheroid cells of approximately 7 to 10μ in diameter that appear to be in all stages of differentiation. These immature cells are round with large nuclei and scant cytoplasm. The nucleus is homogeneous with nucleoli present, while the cytoplasm comprises a fine matrix lacking granulation. In preparations stained with Wright's stain, the stain is light around the nucleus and becomes very dark near the cell membrane. Signet ring cells, which have eccentrically located nuclei and cytoplasmic vacuoles of varying sizes, are also numerous. These appear to be somewhat larger and more lightly staining than the immature cells, and contain easily-stained PAS-positive mucin. The mucin content of the signet ring cells varies from a few PAS-positive granules contained within a large empty "vacuole" to other instances in which the mucin fills the entire cell, pushing aside the nucleus and cytoplasmic contents. Many cells of intermediate size that appear less differentiated also contain varying amounts of PAS-positive material. Mitoses are also common in the cell aggregates and cells containing PAS-positive material have been noted in various stages of mitosis.

C. Cell Cycle Kinetics

Cells were grown in complete medium supplemented with 10 μg/ml bromodeoxyuridine (BrdU) for 49 hours in order to obtain an estimate of the average generation time for TAC-1 cells in culture. The mitotic inhibitor, colcemid, was added for the terminal 3 hours. The tumor cells were harvested by vigorously shaking the flask to loosen the loosely-attached cell aggregates, after which the fibroblast monolayer was washed with medium to remove additional tumor cells. The TAC-1 cells were treated hypotonically with a 1:1 mixture of 0.9% sodium citrate and 0.075M KCl for 10 minutes, after which they were fixed in Carnoy's Fixer (3:1 absolute methanol:glacial acetic acid). After three changes of fixer, the cells were refrigerated overnight prior to dispensing several drops of cell suspension on microscope slides. To achieve differentiation of metaphases that had incorporated BrdU, slides were stained by standard fluorescent plus Giemsa methods. From each culture, 100 metaphases were scored, and the percentage of mitotic figures that had completed 1, 2, or 3 cell divisions in the presence of BrdU was determined. Average generation time (AGT) was estimated as follows (Ivett and Tice, Environ. Mutag. Vol. 4, p. 358, 1982):

$$AGT = (BrdU\ exposure\ time/replicative\ index) \times 100$$

wherein "replicative index"=(1×number of 1st division metaphases)+(2×number of 2nd division metaphases)+(3×3rd division metaphases).

Results of these studies provided an estimate of 45 hours as the average generation time for TAC-1 cells at passage #18. Similar long generation times have been reported for cell lines derived from human adenocarcinoma of the colon. (Leibovitz et al. Cancer Res. Vol. 36, pp. 4562-4569, 1976; and McBain et al., Ibid., 1984).

D. Karyology of Cultured TAC-1 Cells

Preparations of TAC-1 Cells for cytogenetic evaluations were obtained from cultures in their 7th, 10th, 14th, and 17th passage. Colcemid was added directly to the culture flask, or to pooled suspensions of tumor cells that had previously been shaken from the fibroblast monolayer. Cells were incubated at 37° C. for 3-6 hours before harvest and preparation of slide material. The chromosome counts observed at passages 7 and 10 are shown below:

| Passage # | Chromosome Count | | | | |
| --- | --- | --- | --- | --- | --- |
| | <46* | 46* | 55 | 56 | 58 |
| 7 | | 3 | 3 | 2 | |

-continued

| Passage # | Chromosome Count | | | | |
|---|---|---|---|---|---|
| | <46* | 46* | 55 | 56 | 58 |
| 10 | 1 | 1 | 2 | 3 | 1 |

*Metaphases with normal diploid counts presumably derived from normal fibroblasts (i.e., from mitotic "feeder" cells).

At both passages, the modal chromosome number for TAC-1 ranged from 55 to 56, whereas the diploid chromosome complement for the tamarin is 46.

Methods Used to Maintain and Passage TAC-1 Cells

To subculture TAC-1 Cells, spent culture medium containing suspended tumor cells is transferred to sterile centrifuge tubes, and the remaining fibroblast monolayer is washed two times with calcium magnesium-free HBSS. The tumor cells removed during the wash of the fibroblast monolayer are also conserved and pooled with the original cell suspension. Subsequently, 3–4ml of warm 0.25% trypsin (GIBCO 1:250) is washed over the surface of the fibroblast layer for approximately 10–15 seconds. After the trypsin wash, any additional tumor cells that may have been loosened from the fibroblast layer are pooled in the centrifuge tube containing the original spent medium. The fibroblast monolayers are incubated with residual trypsin at 37° C. for 3–4 minutes after which compete medium is added to the flask and the cells are washed down by vigorous pipetting. After a wash in complete medium, ½ of the fibroblast cell suspension and ½ of the tumor cells are dispensed into each of two 25 cm flasks containing 5–7 ml of complete medium. The TAC-1 Cells are subcultured at a ratio of 1:2 at approximately 7–10 days.

Procedure for Cryopreservation of TAC-1 Cells

TAC-1 Cells have been frozen at passages 1, 8, 9, 10, 12, and 15. Cell suspensions of fibroblasts and tumor cells, collected by the procedures described above, are suspended in complete medium containing 7.5% dimethyl sulfoxide. A minimum of $2 \times 10^6$ total cells are dispensed into individual cryotubes which are placed in a styrofoam box for overnight storage at $-70°$ C. Afterwards, the cryotubes are transferred into liquid nitrogen where they are currently maintained. To test for viability after the cells have been subjected to freeze-thaw procedures, we have re-established cultures from frozen cells at passage 8.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A continuous cell line tamarin adenocarcinoma of the colon derived from the species Saquinus oedipus oedipus and designated TAC-1 and deposited with ATCC accession number CRL 10632.

2. A biologically pure culture comprising the cell-line of claim 1 maintained in a suitable medium for growth.

3. The biologically pure culture of claim 2, wherein the medium contains RPMI 1640.

4. The biologically pure culture of claim 3, wherein the medium is a complete medium comprising RPMI 1640 supplemented with 10% fetal bovine serum, 100 units/ml penicillin, 100 µg/ml streptomycin, 2 mM L-glutamine and 2.5 µg/ml fungizone.

* * * * *